United States Patent [19]

Niedbala

[11] Patent Number: 5,017,365

[45] Date of Patent: May 21, 1991

[54] SUNSCREEN COMPOSITION AND APPLICATOR SYSTEM

[75] Inventor: Raymond S. Niedbala, Allentown, Pa.

[73] Assignee: SolarCare Technologies Corporation, Bethlehem, Pa.

[21] Appl. No.: 593,534

[22] Filed: Oct. 3, 1990

Related U.S. Application Data

[63] Continuation-in-part of Ser. No. 191,861, May 9, 1988, abandoned.

[51] Int. Cl.$^5$ .............. A61K 7/42; A61K 7/44; B65D 8/122; B65D 73/00
[52] U.S. Cl. .............. 424/59; 206/205; 206/581; 206/812; 424/60
[58] Field of Search .............. 424/59, 60; 206/581, 206/812

[56] References Cited

U.S. PATENT DOCUMENTS

| | | | |
|---|---|---|---|
| 3,103,682 | 9/1963 | Markle | 15/144 R |
| 3,185,628 | 5/1965 | Fetscher et al. | 424/59 |
| 3,499,575 | 3/1970 | Rockefeller | 206/812 |
| 3,821,363 | 6/1974 | Black | 424/59 |
| 3,912,667 | 10/1975 | Spitzer et al. | 15/104.93 |
| 3,965,518 | 6/1976 | Muoio | 15/104.93 |
| 3,978,204 | 8/1976 | Charle et al. | 15/104.93 |
| 4,069,309 | 1/1978 | Ciaudelli et al. | 424/59 |
| 4,254,102 | 3/1981 | Kaplan | 424/59 |
| 4,299,005 | 11/1981 | Brown | 15/144 R |
| 4,344,930 | 8/1982 | MacRae et al. | 424/59 |
| 4,396,028 | 8/1983 | Waggoner | 15/144 R |
| 4,454,889 | 6/1984 | Contreras, Sr. | 206/581 |
| 4,559,225 | 12/1985 | Fourman | 424/59 |
| 4,683,134 | 7/1987 | Palinczar | 424/59 |
| 4,759,652 | 7/1988 | Ulrich | 15/222 |
| 4,925,029 | 5/1990 | Friedman et al. | 206/581 |

*Primary Examiner*—Dale R. Ore
*Attorney, Agent, or Firm*—Panitch Schwarze Jacobs & Nadel

[57] ABSTRACT

Sunscreen compositions are made capable of rapid, uniform and stable diffusion in emulsified form in fibrous sheet applicator and of drying on the skin to non-tacky, non-greasy films, by emulsifying (1) about 1-25 wt. % of a substantially water-insoluble UV absorbing component capable of absorbing in at least the 290-320 nm range, (2) about 5-20 wt. % of a cosmetically acceptable alcohol, (3) about 1-10 wt. % of a nonionic emulsifier component, (4) about 0.01-0.5 wt. % of a hydrophilic acrylic acid polymer having a molecular weight of at least about $4.5 \times 10^5$, (5) an effective amount of an alkaline neutralizer for the acrylic acid polymer, (6) about 2.5-20 wt. % of an emollient component and (7) at least about 50 wt. % water.

Fibrous sheets impregnated with the compositions can be packaged in vapor-and moisture impermeable containers for stable storage and convenient use.

9 Claims, No Drawings

SUNSCREEN COMPOSITION AND APPLICATOR SYSTEM

This is a continuation-in-part of application Ser. No. 191,861, filed May 9, 1988, now abandoned.

TECHNICAL FIELD

This invention relates to hydroalcoholic sunscreen compositions and a unique applicator system for the compositions. More particularly, the invention concerns sunscreen compositions in emulsion form capable of rapid, uniform and stable diffusion in a fibrous sheet applicator and of drying on the skin to a non-tacky, non-greasy film.

BACKGROUND OF THE INVENTION

Sunscreen compositions depend for their efficacy on ultraviolet light absorbing chemical agents to block the erythemal (skin reddening) wave lengths of ultraviolet radiation. Zinc oxide, titanium dioxide and talc are representative of physical sun blocking agents and p-aminobenzoic acid (PABA) and its derivatives are representative of chemical sunscreen agents. An ideal sunscreen agent has a high extinction coefficient (absorptivity), and is non-photosensitizing, chemically stable, non-toxic and non-irritating. In addition, if it is desired to minimize washing off of the sunscreen composition while swimming or as the result of perspiration, sunscreen agents which are substantive to the skin are preferred over less water-resistant sunscreen compositions. Because sunscreens presently approved by the FDA are not by themselves substantive, carrier vehicles must be selected which increase substantivity. In many cases these are emulsions. If the vehicles are oil-based, the resulting composition necessarily will be oily and often tacky, characteristics which are usually undesirable. If, on the other hand, the vehicle is an oil in water emulsion, the result will be more elegant. Accordingly, careful attention in formulating is required in order to incorporate all ingredients uniformly into the composition and to form a stable emulsion.

The mode of application of the sunscreen composition imposes additional requirements on the sunscreen formulation. While application by hand, swab or spray is generally in use, it is now proposed, in accordance with the present invention, to apply a substantive sunscreen composition from a fibrous sheet uniformly impregnated with the composition and prepackaged in a vapor-and-water impermeable container such as a polyethylene envelope. Fibrous sheet applicator systems require, however, that a composition have a low viscosity for rapid and uniform diffusion throughout the applicator prior to packaging. Low viscosity in turn suggests that the composition have a high water and/or alcohol content. However, it is difficult to form stable emulsions of low viscosity sunscreen dispersions. Moreover, too much alcohol may destabilize emulsions and cause a burning sensation and undesirable drying of the skin. Too little alcohol reduces solvency and/or emulsifiability of some active ingredients in sunscreen compositions and dispersibility of the formulation in the fibrous sheet applicator. Nevertheless, a cosmetically acceptable alcohol is desirable in a sunscreen composition to aid in lowering the viscosity, to decrease the drying time, and to improve the feel of the composition (including the cooling effect resulting from evaporation).

A variety of sunscreen compositions have been developed as well as devices and materials for applying the products. For example, U.S. Pat. No. 4,559,225 to Fourman discloses a non-aqueous sunscreen composition containing 10-90 wt. % alcohol and a film-forming cellulosic polymer to render the composition resistant to removal by water.

U.S. Pat. No. 4,254,102 to Kaplan et al. describes the enhancement of substantivity of a sunscreen composition to wet skin by the incorporation of 2-6 wt. % of a solid fatty alcohol such as cetyl alcohol. The composition contains 45-65 wt. % water.

U.S. Pat. No. 4,069,309 to Ciaudelli et al. describes certain cationic para-amino benzoate esters which improve the resistance of sunscreen compositions to removal by moisture. Formulations are described containing water/alcohol proportions of 30/70 and 50/50 by weight.

U.S. Pat. No. 4,683,134 to Palinczar describes sunscreen compositions based upon a neutralized, cross-linked acrylic polymer, up to 90% by weight alcohol, an ethyoxylate fatty amine as a neutralizing agent for the polymer, and 2-10% by weight of water.

U.S. Pat. No. 3,185,628 to Fetscher et al describes sunscreens containing sulfone derivatives as the sunscreen agent. The compositions are emulsions. Example IX discloses a composition containing 50 wt. % alcohol and 45 wt. % water and Example X shows a composition containing no alcohol and 62 wt. % water.

U.S. Pat. No. 3,821,363 to Black et al. describes sunscreen gels based upon ethylene maleic acid anhydride copolymers. The formulations may contain 45-55 wt. % alcohol and 46-80 wt. % water (clear) or the same amount of water with no alcohol (opaque).

U.S. Pat. No. 3,103,682 to Markle discloses the application of suntanning oils or creams with an absorbent pad such as a plastic sponge.

The article "Sunscreen and Suntan Products" *Handbook of Non-Prescription Drugs, American Pharmaceutical Association,* by E. M. De Simone II, Chap. 26, pages 499-511, describes a variety of sunscreen formulations and selection criteria. The disclosures of this article and of the patents cited in this specification are incorporated herein by references.

It is known to incorporate cosmetic and therapeutic compositions, including emulsions thereof, into fibrous articles or sheets and to package the articles in vapor- and moisture-resistant containers such as polyethylene envelopes and the like, as described in U.S. Pat. Nos. 4,559,157, 2,999,265, 2,840,080, 3,624,224 and 3,896,807. Nevertheless, no high water content sunscreen agents, so far as is known, have been formulated specifically for application with a fibrous sheet material wherein the fibrous sheets are impregnated with the formulation and prepackaged in vapor-and moisture-impermeable containers.

SUMMARY OF THE INVENTION

It has now been found that by critically selecting the ingredients and proportions of a sunscreen composition, a high water content aqueous based emulsion can be formulated which will absorb quickly and uniformly in a fibrous sheet. It has also been found that the fibrous sheet will itself enhance the stability of the composition so that when packaged in a vapor-and moisture-impermeable container, the product will have a satisfactory shelf life and can be applied conveniently and effectively as needed.

The sunscreen compositions of the invention have a low viscosity, as represented by a specific gravity of 0.90–1.05, preferably 0.95–1.00, and comprise an aqueous based emulsion of:

(1) about 1–25 wt. % of a substantially water insoluble UV-absorbing component capable of absorbing in at least the 290–320 nm range;

(2) about 5–20 wt. % of a cosmetically acceptable alcohol;

(3) about 1–10 wt. % of a nonionic emulsifier component;

(4) about 0.01–0.5 wt. % of a hydrophilic acrylic acid polymer having a molecular weight of at least about $4.5 \times 10^5$;

(5) an effective amount of an alkaline neutralizer for the acrylic acid polymer;

(6) about 2.5–20 wt. % of an emollient component; and (7) at least about 50 wt. % water.

When so formulated, the composition is capable of rapid, uniform and stable diffusion throughout a fibrous sheet applicator and of drying on the skin to a non-tacky, non-greasy film supplying an SPF (Sun Protection Factor) determined primarily by the active sunscreen agents incorporated into the composition. SPF is the ratio of the minimum erythemal dose (MED) of protected skin to the MED of unprotected skin. MED is the least exposure dose of radiation at a specified wavelength that will elicit a delayed erythema response. The higher the SPF, the more effective the agent in preventing sunburn, but the less the chance of developing a slow natural tan. The sunscreen compositions of the invention can be prepared with any SPF, e.g., 2–15 or higher.

DETAILED DESCRIPTION

The UV absorbing component comprises one or more compounds known for efficacy as sunscreen agents. Because the UV-B band (290–320nm) of the UV spectrum produces the most severe erythema (sunburn), a major proportion of the UV-absorbing component will be one or more compounds which absorb in the UV-B range. Such compounds include the following (which are also recommended as being safe by an FDA advisory review panel—Federal Register, 43, 38219–38253, 1978):

---

Aminobenzoic acid (para-isomer)
Cinoxate (2-ethoxyethyl p-methoxycinnamate)
Diethanolamine p-methoxycinnamate
Digalloyl trioleate
Dioxybenzone (2,2'-dihydroxy-4-methoxybenzophenone)
Ethyl 4-[bis(hydroxypropyl)] aminobenzoate
2-Ethylhexyl 2-cyano-3,3-diphenylacrylate
Ethylhexyl p-methoxycinnamate
2-Ethylhexyl salicylate
Glyceryl aminobenzoate
Homosalate (homomethyl salicylate)
Lawsone with dihydroxyacetone
Mentyl anthranilate
Oxybenzone (2-hydroxy-4-methoxy-benzophenone)
Padimate A
Padimate O
2-Phenylbenzimidazole-5-sulfonic acid
Sulisobenzone (2-hydroxy-4-methoxy-benzophenone-5-sulfonic acid)
Triethanolamine salicylate

---

Other sunscreen compositions having maximum absorbence outside of UV-B band may be employed in minor amounts in the UV-absorbing component depending upon their safety as determined by applicable governmental standards. Candidate compounds include the class of 2,2'-dihydroxy diphenyl sulfones described in U.S. Pat. No. 3,185,628 and the dialkyl amino benzoic acid esters containing a quaternary amine in the ester group described in U.S. Pat. No. 4,069,309. Generally, the UV-absorbing component will be selected for its ability to absorb radiation in at least the UV-B band and to transmit radiation in at least the UV-A band in order to avoid substantial sunburn while inducing tanning. The UV absorbing component is used in an amount of about 1–25 wt. %, preferably about 5–20 wt. %, based on total weight of the sunscreen composition and desired SPF rating.

The preferred UV absorbing compounds are ethylhexyl p-methoxycinnamate (2–7.5 wt. %), octyl dimethyl p-aminobenzoic acid (1–8 wt. %) and oxybenzone (2–8 wt. %), either singly or in mixtures of two or more thereof, the weight being based on weight of total sunscreen composition.

The other active ingredients of the composition include a hydrophilic acrylic acid polymer, an alkaline neutralizer for the acrylic acid polymer, and an emollient component. The acrylic acid polymer is a skin lubricant, a dispersant for the UV-absorbing component and emollient, and also enhances the stability of the emulsion. The acrylic acid polymers comprise a class of well known cosmetically acceptable materials, sometimes identified as "carboxy polymethylenes" or "carbomers", and are commercially available under the trademark and designation "Carbopol" (B.F. Goodrich). The polymers have molecular weights of at least about $4.5 \times 10^5$, ranging generally up to about $4 \times 10^6$. The lower molecular weight polymers in the series are linear and have the highest water solubility without appreciably increasing the viscosity of the medium in which they are used. The higher molecular weight polymers are crosslinked with a polyalkenyl polyether and supply increasing thickening efficiencies. The preferred polymer is Carbopol ® 934, a crosslinked water soluble resin having a molecular weight of about $3 \times 10^6$. The amount of the acrylic acid polymer used in the composition depends in part upon the molecular weight of the polymer, smaller amounts of a higher molecular weight polymer being useful, and vice versa. Generally, the acrylic acid polymers are used in amounts of about 0.01–0.5 wt. % of the total sunscreen composition, and preferably in the range of about 0.015–0.1 wt. % on the same basis.

The neutralizer is added to the composition in amounts effective to neutralize the acrylic acid polymer. Generally, therefore, the acrylic polymer and neutralizer will be present on a 1:1 equivalent weight basis or other proportion in order to obtain a desired pH. Any compound compatible with the other components of the composition may be used as the neutralizer, including both inorganic bases (such as alkali metal hydroxides) and organic materials such as alkyl amines, polyamines and quaternary ammonium compounds. A preferred neutralizer is polyoxyethylene cocoamine, a class of ethoxylated fatty amines wherein the water solubility depends upon the degree of ethoxylation, suitable ethoxylation being about 5–20, preferably about 15. The ethoxylated fatty amines function not only as neutralizers but also as secondary emulsifiers in the compositions and improve the substantivity of the composition to the skin. About 0.05–0.5 wt. % of the ethoxylated fatty amine is preferred.

The sunscreen compositions also contain an emollient in an amount of about 2.5–20 wt. %, preferably about 5–15 wt. %, based on total composition weight. Any emollients may be used, including hydrocarbon oils and waxes; fatty acid esters of low molecular weight alcohols, such as butyl stearate, isopropyl stearate and isopropyl palmitate; fatty alcohols of about 12–18 carbon atoms; stearates of polyhydroxy compounds, such as glyceryl stearate; alkoxylated olefins such as polyoxypropylene butyl ether and polyoxypropylene cetyl ether; and silicones such as methyl phenyl polysiloxane of which phenyltrimethicone (Dow Corning 556 fluid) used at about 1.0–5.0 wt. % is representative. The emollient is selected to avoid a greasy, tacky feeling and for this reason the preferred emollients are polyhydroxy alcohol esters of fatty acids, such as glyceryl stearate (0.5–5 wt. %); fatty alcohols such as isostearyl, cetyl and oleyl alcohol (5–10 wt. %); and the phenyl methyl polysiloxanes (1.0–5.0 wt. %). The emollients may be used singly or in combination of two or more.

The nonionic emulsifiers useful in the compositions of the invention are any cosmetically acceptable nonionic surfactants, the most important class being the ethoxylates. Generally, the ethoxylates are condensates of ethylene oxide and a hydrophobic compound containing an active hydrogen atom. The hydrophile-lipophile balance (HLB) of these nonionic surfactants generally range about 7–18 wherein the HLB number is calculated from HLB=E/5 where E is the weight percentage of ethylene oxide in the molecule. The ethoxylates include fatty alcohol ethoxylates; alkylphenol ethoxylates wherein the alkyl group typically is octyl or nonyl; glycerol esters including saturated and unsaturated fatty acid mono- and diglycerides and mixtures thereof; polyoxyethylene esters prepared by condensing polyethylene glycol with fatty acids or aliphatic carboxylic acids related to abietic acid; anhydrosorbitol esters including mono-, di-, and tri-esters of sorbitan and fatty acids; ethoxylated anhydrosorbitrol esters prepared by ethoxylation of sorbitan fatty acid esters; and ethoxylated natural fats, oils and waxes such as ethoxylated castor oil. Other nonionic emulsifiers include glycol esters of fatty acids, such as ethylene glycol, diethylene glycol and 1,2-propane diol esters of fatty acids; carboxylic amides such as diethanolamine condensates of fatty acids; monoalkanolamine condensates of fatty acids; and ethoxylated fatty acid amides; and the polyalkylene oxide block copolymers such as the poly(oxyethylene-co-oxypropylene) surfactants available from various sources.

The foregoing and other nonionic emulsifiers are commercially available and are described in the technical literature such as Kirk-Othmer, *Encyclopedia of Chemical Technology*, 3rd Edition, 22 360–377, incorporated herein by reference.

The preferred class of nonionic emulsifiers for use in the invention are the ethoxylates of which the fatty alcohol ethoxylates and alkylphenol ethoxylates are representative, the preferred amount being 1.0–5.0 wt. % on total composition. Polyoxyethylene (21) stearyl ether, wherein the numeral refers to the number of ethylene oxide units in the molecule, is the most preferred emulsifier.

The nonionic emulsifier is present in the composition in an amount of about 1–10 wt. %, preferably about 1–5 wt. %, based on total weight of the composition. The emulsifiers may be used singly or in mixtures, one such mixture being a blend of fatty alcohol ethoxylate and ethoxylated sorbitan ester sold by Croda, Inc. under the trademark and designation "Polawax". Because of their fatty acid and/or fatty alcohol content, many of the nonionic emulsifiers also function as emollients, emulsion stabilizers, couplers, lubricators and viscosity modifiers.

The vehicle for the active ingredients of the composition further includes a cosmetically acceptable alcohol such as ethanol and isopropanol, including mixtures thereof. A suitable grade is SDA-40, including variations within the grade, such as anhydrous and 190 proof. The alcohol component decreases drying time, aids in dispersion of the active ingredients in the composition and diffusion of the composition in the fibrous sheet applicator, and improves feel of the composition on the skin. From about 5–20 wt. % of the alcohol is used in the formulation, preferably about 5–10 wt. %, based on total weight of the composition. Higher amounts will destabilize the emulsion and lower amounts may be insufficient to help solubilization of the UV-absorbers and to contribute to a good hand.

Water (preferably deionized) comprises the final essential component of the composition, sufficient water being present to make 100 wt. % total composition. Generally, water will comprise at least about 50 wt. % of the composition, e.g., about 50–75 wt. %.

Other ingredients may be present in the composition for special properties. These include spreading and waterproofing properties, achievable by a polysiloxane such as polyphenylmethyl siloxane copolymer, preservatives such as Quaternium 15 (Dowacil 200) available from Dow Corning and Dow Chemical Company, respectively, and methyl or propyl paraben. Other optional ingredients include fragrancies and cationic or anionic emulsifiers (in amounts less than the amount of nonionic emulsifier in order to avoid washing off too easily). Still other optional ingredients are physical sunblocking agents such as zinc oxide or titanium dioxide, humectants such as polyoxyethylene adipate, and thickeners such as water soluble cellulosic polymers of which hydroxypropyl cellulose, hydroxyethyl cellulose and methyl cellulose are representative. The cellulosic polymers also aid in film formation.

The compositions of the invention are generally prepared by slowly adding the acrylic polymer to the water while gently stirring and heating at about 65°–70° C. Separately, a solution is formed of the emollient and secondary emulsifiers, if any, under generally the same conditions. The two solutions are mixed at the appropriate temperature with stirring and then heat is removed. The neutralizing agent is then added to the mixture. In a separate vessel, the UV-absorbing component and the alcohol are mixed and heated gently to dissolve. The resulting mixture is then added to the previously prepared mixture at below about 40° C. with suitable stirring, followed by addition of preservative. When the resulting emulsion cools to room temperature, it is capped and ready for storage. The proportions of the ingredients are such as to provide a specific gravity of 0.90–1.05, preferably 0.95–1.00.

If desired, the emulsion may be encapsulated in polymer microspheres in the manner described in U.S. Pat. No. 4,690,825 (Chemical Week, Mar. 9, 1988, page 16) prior to application to the fibrous sheet material. The encapsulating polymer is selected to permit release of the active ingredients by pressure of the fibrous applicator on the skin, by subsequent rubbing of the sunscreen composition on the screen, by the heat of the sun or by any combination of these mechanisms.

To prepare the applicator systems of the invention, the sunscreen composition is added in any suitable manner to a soft, pliable fibrous sheet material formed from any suitable woven or nonwoven fiber or fiber mixture having sufficient wet strength and absorbency to hold an effective sunscreen amount of the composition. The fibrous material includes both natural and synthetic materials such as cotton, hemp, airlayed cellulose, polyester, polypropylene, nylon, rayon and the like, including blends thereof such as rayon/polypropylene, rayon/cellulose, polyester/cellulose, polyester/rayon, and the like. A particularly effective fibrous sheet is airlayed wood pulp containing a binder which when processed creates a network of air pockets, resulting in greatly increased absorbency. This material is available from the Fort Howard Paper Company, Green Bay, Wis. The fibrous sheet applicator may also comprise a biodegradable material in order to reduce disposal problems.

After dispersion of the composition in the fibrous sheet, the product is packaged in any of the moisture-and-vapor impermeable containers known in the art including polyethylene envelopes, resealable packages of all types (such as packages provided with zip locks), plastic tubs and the like, such as are described in U.S. Pat. Nos. 2,999,265; 2,284,080; and 4,559,157. When thus supported and packaged, the sunscreen composition provides a portable, disposable, low weight, no-leak system for sunscreen application under various conditions of use. The system is used by tearing or otherwise opening the container and applying the sunscreen by wiping action of the fibrous applicator on the skin.

The following will serve as further illustration of the invention. However, the invention is not limited to the examples or other details set forth, and it will be appreciated that various other embodiments and modifications are equivalent for the stated and illustrated functions without departing from the spirit and scope of the invention.

EXAMPLE 1

A sunscreen composition in emulsion form having an SPF of about 15 was prepared from the following formulation:

| No. | Ingredients | % w/w |
|---|---|---|
| 1 | Distilled water | 59.5 |
| 2 | Carbomer 934 resin | 0.021 |
| 3 | Ethanol, SDA 40 | 10.0 |
| 4 | Oxybenzone | 3.0 |
| 5 | Phenyltrimethicone | 5.0 |
| 6 | Octyl Methoxycinnamate | 7.5 |
| 7 | Octyl Dimethyl PABA | 8.0 |
| 8 | Polyoxyethylene (21) stearyl ether | 2.5 |
| 9 | Isostearyl Alcohol | 5.0 |
| 10 | Glyceryl Stearate | 1.4 |
| 11 | Self Emulsifying Wax | 1.4 |
| 12 | Ethoxylated (15) cocoalkylamine | 0.2 |
| 13 | Quaternium 15 | 0.1 |

Ingredient 2 is a polyalkenyl polyether-crosslinked acrylic polymer available from B.F. Goodrich as "Carbopol 934" water soluble resin having a molecular weight of $3 \times 10^6$. Ingredient 5 is a polyphenylmethylsiloxane copolymer sold by Dow Corning as "Dow Corning 556 Fluid". Ingredient 6 is an abbreviation for ethylhexyl p-methoxycinnamate. Ingredient 7 is an abbreviation for octyldimethyl para-aminobenzoic acid. Ingredient 11 is a mixture of a fatty alcohol ethoxylate and ethoxylated sorbitan esters sold as "Polawax" by Croda. Ingredient 13 is a preservative sold by Dow Chemical.

The formulation was prepared as follows. With gentle stirring ingredients 1 and 2 are mixed and heated to 65°-70° C. In a separate vessel ingredients 8-11 are mixed gently with stirring and heating to 65°-70° C. Then the first mixture is added to the second with continued stirring at 65°-70° C. Heat is then removed and ingredient 12 is added with stirring. In a separate container ingredients 3-8 are mixed and heated gently to dissolve. The prior mixture is cooled to below 40° C. and the mixture of ingredients 3-8 is added with continued stirring. Lastly, ingredient 13 is added with stirring. When the resulting opaque, slightly yellow emulsion cools to room temperature, it may be stored. The emulsion when applied to skin dries quickly without an offensive alcohol odor and leaves a dry, non-tacky film.

The formulation was compared to commercial sunscreen formulations and the formulation of the Example of U.S. Pat. No. 4,254,102 for ability to distribute throughout a fibrous sheet. In the test, a 7×7 inch piece of airlaid cellulose (Howard Paper Co.) towel was cut and placed on wax paper. To the center of the towel, 10 grams of each preparation was applied. After 30 minutes at room temperature the area of migration for each formula was outlined and the percent of distribution calculated as shown below. The results are given in Table 1. It can be seen that the formulation of the invention diffused effectively in the sheet whereas the other products resisted diffusion.

TABLE 1

Percent Distribution = Area of Migration = Initial Area Covered × 100
Total Area

| Formula | Percent Distribution | Area (Start) | Area (Finish) |
|---|---|---|---|
| 1. Formula of Example 1 Estimated SPF 15 | 84 | 1" × 1" | 6" × 7" |
| 2. Block Out, Sea and Ski Products SPF 25 | 0 | 1.75" × 2" | Same |
| 3. Coppertone Sunblock Lotion SPF 25 | 0 | 1.5" × 1.8" | Same |
| 4. Block Out, Sea and Ski | 0 | 1.8" × 1.6" | Same |
| 5. Ultra Shade, Plough Inc. | 0 | 1.6" × 1.1" | Same |
| 6. Kaplan et al U.S. Pat. No. | 0 | 2.5" × 2.0" | Same |

TABLE 1-continued

Percent Distribution = Area of Migration = Initial Area Covered × 100
Total Area

| Formula | Percent Distribution | Area (Start) | Area (Finish) |
|---|---|---|---|
| 4254102 | | | |

EXAMPLE 2

The following sunscreen formulations were prepared essentially as described in Example 1. Formulation A is a formulation of the invention. Formulation B is similar to formula A but its high alcohol content and lack of Carbomer take it out of the scope of the invention:

| | % w/w |
|---|---|
| Distilled water | 62.5 |
| Carbomer 934 | 0.021 |
| Ethoxylated cocoalkylamine | 0.2 |
| Ethanol | 10.0 |
| Oxybenzone | 3.0 |
| Glyceryl Stearate | 1.25 |
| Octyl Methoxycinnamate | 7.5 |
| Octyl Dimethyl PABA | 8.0 |
| Polyoxyethylene (21) stearyl ether | 2.5 |
| Isostearyl Alcohol | 5.0 |
| Quarternium 15 | 0.1 |

Formulation B

| | % w/w |
|---|---|
| Oxybenzone | 3.0 |
| Ethyl dihydroxypropyl PABA | 5.0 |
| Octyl dimethyl PABA | 8.0 |
| Propylene Glycol | 5.0 |
| Methyl paraben | 0.5 |
| Propyl paraben | 0.5 |
| Lanolin | 2.0 |
| Ethoxylated glucose ether | 5.0 |
| Ethanol | 55 |
| Distilled water | 8.0 |
| Glycerine | 8.0 |
| Fragrance/preservatives | qs |

Although formulations A and B each provide an SPF of about 15, formulation A dries quickly to a non-tacky, non-greasy film without the offensive odor of alcohol, whereas formulation B not only has an offensive alcohol odor but also is flammable, has low moisturizing properties and dries to a sticky, tacky film. Formulation A is quickly absorbed by a fibrous sheet applicator and does not separate from the sheet when stored at 37° C. for three weeks. No separation in the emulsion (not applied to the sheet) was observed over the same period. Similar stability was also observed for Formulation B. However, because of the high concentration of alcohol, formulation B dried onto the applicator when left standing.

EXAMPLE 3

The ability of formulation A of Example 2 to distribute in several different types of fibrous sheets was evaluated as compared to the formula of the Example of U.S. Pat. No. 4,254,102 to Kaplan et al. In the test, a 2×2 inch swatch of each fibrous material was placed on a flat surface backed by plastic. Two grams of each formula was applied to the center of different samples of the material. A photo was taken immediately after application and twenty minutes later. The area of migration was outlined and calculated. The results are shown in Table 2 below from which it will be seen that in all cases the formulation of the invention was absorbed quickly and extensively in the sheet whereas the Kaplan et al formulation did not migrate at all in the allotted time (20 minutes). The fibrous sheet materials are products of Howard Paper Company, Green Bay, Wisconsin. As described in Example 2, formulation A was stable on the applicator at elevated temperature. The Kaplan et al formulation could not be tested in the same manner since it did not absorb into the applicator material.

TABLE 2

| I. Air layed non-woven cellulose. | | |
|---|---|---|
| Typical Properties | Grade 804 | Grade 839 |
| Thickness | 0.001 in | 0.001 |
| Dry Tensile, g/in MD | 1655 | 1120 |
| Wet Tensile, g/in MD | 555 | 575 |
| Absorbent capacity, XOW | 14 | 14.5 |
| Absorbency rate (seconds) | 2 | 4 |
| Test Results | | |
| Area of Migration | | |
| Formulation A | 95% | 97% |
| Kaplan et al formulation | 0 | 0 |
| II. Synthetic Rayon Fabrics | | |
| Typical Properties | Grade 916 | Grade 997 |
| Thickness | 0.013 | 0.011 |
| Dry Tensile, g/in MD | 3000 | 5500 |
| Wet Tensile, g/in MD | 1350 | 2000 |
| Absorbent Capacity, XOW | 8.1 | 5.5 |
| Absorbency rate | 1.2 | 2.0 |
| Test Results | | |
| Area of Migration | | |
| Formulation A | 100% | 100% |
| Kaplan et al formulation | 0 | 0 |

It appears from the test results that the high concentration of water and alcohol in formulation A aids in the distribution through the absorbent materials. The water phase may also bind to regions of the absorbent material and thus prevent immobilization of active ingredients. This was demonstrated by SPF determinations on formulations of the invention on and off the sheets since formulation A did not show signs of separation on the sheet even after several weeks at elevated temperature.

I claim:

1. A sunscreen package comprising a fibrous sheet impregnated with a sunprotective, aqueous based emulsion, said impregnated sheet incorporated in a vapor and moisture impermeable container, said aqueous based emulsion having a specific gravity of 0.90–1.05 and comprising:
 (1) about 1–25 wt. % of a substantially water insoluble UV absorbing component capable of absorbing in at least the 290–320 nm range;
 (2) about 5–20 wt. % of a cosmetically acceptable alcohol;
 (3) about 1–10 wt. % of a nonionic emulsifier component;

(4) about 0.01–0.5 wt. % of a hydrophilic acrylic acid polymer having a molecular weight of at least about $4.5 \times 10^5$;

(5) an effective amount of an alkaline neutralizer for the acrylic acid polymer;

(6) about 2.5–20 wt. % of an emollient component; and (7) at least about 50 wt. % water.

2. The package of claim 1 wherein the cosmetically acceptable alcohol is ethanol.

3. The package of claim 1 wherein the UV-absorbing component (1) of the emulsion is selected from at least one of ethylhexyl p-methoxycinnamate, octyl dimethyl p-aminobenzoic acid and oxybenzone.

4. The package of claim 1 wherein the nonionic emulsifier (3) of the emulsion is a fatty alcohol ethoxylate.

5. The package of claim 1 wherein the neutralizer (5) of the emulsion is a polyoxyethylene cocoamine.

6. The package of claim 1 wherein the nonionic emulsifier (3) of the emulsion comprises about 1–5 wt. %, the acrylic acid polymer (4) comprises about 0.015–0.1 wt. % and the emollient (6) comprises about 5–15 wt. %.

7. The package of claim 1 wherein the nonionic emulsifier (3) is a polyoxyethylene stearyl ether, and the alkaline neutralizer (6) is a polyoxyethylene cocoamine.

8. The package of claim 1 wherein the UV absorbing component (1) is selected from at least one of ethylhexyl p methoxycinnamate, octyl dimethyl p-aminobenzoic acid and oxybenzone, the nonionic emulsifier (3) is a fatty alcohol ethoxylate, the molecular weight of the acrylic acid polymer is about $4.5 \times 10^5$ to $5 \times 10^6$, the neutralizer (5) is a polyoxyethylene cocoamine, and the emollient (6) is selected from at least one of a fatty alcohol, a fatty acid glyceride and a polysiloxane.

9. The package of claim 8 wherein the fatty alcohol (6) is cetyl alcohol or isostearyl alcohol, the fatty acid glyceride is glyceryl stearate and the polysiloxane is methylphenyl polysiloxane.

* * * * *